United States Patent [19]

Wilk et al.

[11] Patent Number: 5,236,455
[45] Date of Patent: Aug. 17, 1993

[54] TYMPANIC PATCH, APPLICATOR, AND RELATED METHOD

[76] Inventors: Peter J. Wilk, 185 W. End Ave., New York, N.Y. 10023; James Z. Cinberg, 167 N. Ridgewood Rd., South Orange, N.J. 07079

[21] Appl. No.: 832,918

[22] Filed: Feb. 10, 1992

[51] Int. Cl.⁵ .............................. A61F 2/18
[52] U.S. Cl. ...................... 623/10; 623/11; 602/58; 606/107; 606/109; 128/890
[58] Field of Search ............. 128/890, 893, 894, 887; 623/10, 11; 602/52, 57, 58; 606/107, 109

[56] References Cited

U.S. PATENT DOCUMENTS

| | | |
|---|---|---|
| 3,530,860 | 9/1970 | Majoros . |
| 4,047,532 | 9/1977 | Phillips et al. ............. 606/107 |
| 4,865,026 | 9/1989 | Barrett ..................... 602/58 |
| 5,026,378 | 6/1991 | Goldsmith, III . |

FOREIGN PATENT DOCUMENTS

| | | | |
|---|---|---|---|
| 0399782 | 11/1990 | European Pat. Off. .......... 623/10 |
| 2441381 | 7/1980 | France .................... 623/10 |
| 2627079 | 8/1989 | France .................... 623/10 |

Primary Examiner—Randall L. Green
Assistant Examiner—Paul Prebilic
Attorney, Agent, or Firm—R. Neil Sudol; Henry D. Coleman

[57] ABSTRACT

A device for repairing a tympanic membrane comprises a patch provided on one side with an adhesive layer, and an elongate tubular applicator member having a proximal end and a distal end. The patch is removably attached via suction to the distal end of the tubular applicator member so that the adhesive layer faces away from the elongate applicator member. The proximal end of the tubular applicator member is temporarily closed or sealed to maintain the suction force, thereby holding the tympanic patch to the distal end of the applicator tube while the tube is being inserted through the auditory canal. Upon a pressing of the patch against the ear drum so that the patch covers the perforation, the proximal end of the tube is released to pressurize the tube channel with ambient air. This pressurization releases the patch and allows it to adhere to the tympanic membrane.

9 Claims, 2 Drawing Sheets

TYMPANIC PATCH, APPLICATOR, AND RELATED METHOD

BACKGROUND OF THE INVENTION

This invention relates to patch for repairing a perforation in a tympanic membrane. This invention also relates to an applicator device for applying the patch to a patient's tympanic membrane. In addition, this invention relates to an associated method for repairing a perforated tympanic membrane.

Tympanic perforations can lead to inner ear infections, for example, if fluid from the outer ear leaks through a perforation into the inner ear. In addition, a perforation in a tympanic membrane results in hearing losses.

The conventional procedure for repairing a hole in an ear drum is to pull skin tissue from the side of the auditory canal over the perforation. This procedure, however, is not possible for various elderly patients.

OBJECTS OF THE INVENTION

An object of the present invention is to provide a method and an associated apparatus for repairing a perforated tympanic membrane.

Another object of the present invention is to provide such a method and associated apparatus which can be used to repair perforated tympanic membranes of elderly patients.

Another, more particular, object of the present invention is to provide such a method and associated apparatus which are easy to use.

A further particular object of the present invention is to provide such an apparatus or device which is easy and inexpensive to manufacture.

SUMMARY OF THE INVENTION

A device for repairing a tympanic membrane comprises, in accordance with the present invention, a patch provided on one side with a fastening element for securing the patch to a tympanic membrane, and an elongate applicator member having a proximal end and a distal end. The patch is removably attached to the distal end of the elongate applicator member so that the fastening element faces away from the elongate applicator member.

Preferably, the fastening element takes the form of an adhesive layer. Also, it is preferable that the patch is circular. In that event, the adhesive layer may take an annular form.

Alternatively, or additionally, the fastening element takes the form of a plurality of barbs, teeth, or similar features which point away from the patch.

According to another feature of the present invention, the repair device further comprises an element for removably attaching the patch to the distal end of the elongate applicator member. Such an element may take the form of an auxiliary adhesive layer on the other side of the patch. That auxiliary layer then has an adhesiveness which is less than the adhesiveness of the first layer.

Alternatively, the elongate applicator member may take the form of a tube. In that event the element for removably attaching the patch to the distal end of the applicator member includes an elongate channel which extends longitudinally through the tube and which is susceptible to the application of suction. In use, the patch is positioned at the distal end of the applicator tube. Suction is then applied at the proximal end of the tube. The proximal end is temporarily closed or sealed to maintain the suction force, thereby holding the tympanic patch to the distal end of the applicator tube while the tube is being inserted through the auditory canal. Upon a pressing of the patch against the ear drum so that the patch covers the perforation, the proximal end of the tube is released to pressurize the tube channel with ambient air. This pressurization releases the patch and allows it to adhere to the tympanic membrane.

Pursuant to a further feature of the present invention, the elongate applicator member is formed at the distal end with an enlarged terminal portion. The terminal portion may have an annular surface, the patch being removably attached to the annular surface.

Pursuant to an additional feature of the present invention, the elongate applicator member is made of a material such as a metal or alloy having a limited malleability. Accordingly, the applicator member (whether a tube or a rod) may be reconfigured prior to the application of the patch, thereby facilitating the positioning of the patch over the perforation in the tympanic membrane.

An article for repairing a tympanic membrane comprises, in accordance with the present invention, a patch having a diameter less than three millimeters, the patch being provided on one side with an adhesive layer. Preferably, the patch is circular. In that event, the adhesive layer may take an annular form.

A method for repairing a perforation in a tympanic membrane comprises, in accordance with the present invention, the steps of (a) providing a patch having a fastening element on one side, and (b) applying the patch to the tympanic membrane so that the fastening element engages the membrane in region surrounding the perforation in the membrane.

Preferably, the fastening element takes the form of an adhesive layer. Alternatively, or additionally, the fastening element may include a plurality of barb-like features.

The step of applying the patch preferably comprises the step of pressing the patch to the membrane with an elongate applicator member. The patch is removably attached, prior to the application of the patch to the tympanic membrane, to the distal end of the elongate applicator member so that the adhesive layer faces away from the elongate applicator member.

The step of applying the patch further includes the step of inserting the distal end of the elongate applicator member into the auditory canal of a patient towards the tympanic membrane to be repaired. The patch is attached to the distal end of the elongate applicator member prior the insertion of the applicator member into the auditory canal.

According to another feature of the present invention, the elongate applicator member is in the form of a tube having a proximal end and a distal end. Then, the step of attaching the patch to the applicator member includes the step of applying suction to the tube to hold the patch to the distal end thereof. The step of applying also includes the step of removing the suction on the tube upon initiation of the step of pressing.

Where the elongate applicator member is made of a material having a limited malleability, the method further comprises the step of bending the elongate applicator member prior to the step of inserting, thereby optimizing a positioning of the patch over the perforation in the tympanic membrane.

A method and an associated apparatus for repairing a perforated tympanic membrane in accordance with the present invention can be used to repair perforated tympanic membranes of elderly patients. The method is easy to use. Moreover, the applicator tube and patch are easy to manufacture.

DETAILED DESCRIPTION

Figure 1:
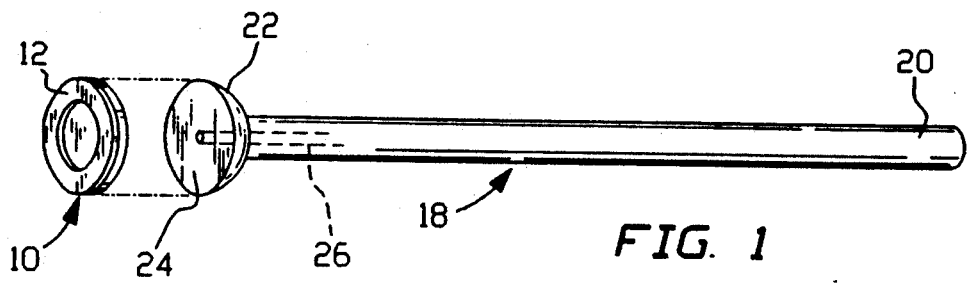
FIG. 1 is a schematic side perspective view, on an enlarged scale, of a tympanic patch and an applicator member in accordance with the present invention.
Figure 5:
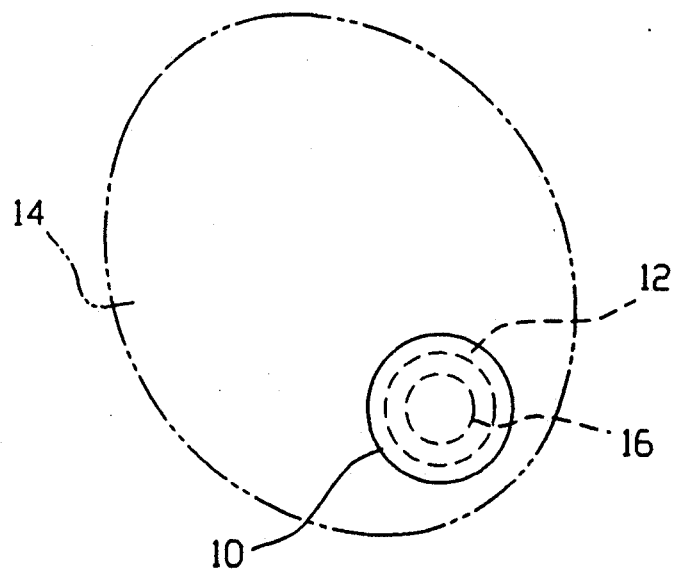
FIG. 5 is a schematic elevational view, on an enlarged scale, of a tympanic patch in accordance with the present invention, in place on a tympanic membrane.

As illustrated in FIG. 1, a device for repairing a perforated tympanic membrane comprises a circular patch 10 provided on one side with an annular adhesive layer 12. Patch 10 is small and has a diameter less than three millimeters. During a surgical repair operation, patch 10 is affixed to a tympanic membrane 14 (FIG. 5) over a perforation 16 (FIG. 5) via an elongate applicator member 18 in the form of a tube having a proximal end 20 and an enlarged distal end or terminal portion 22. Patch 10 is removably attached to the distal end of the applicator tube 18 so that adhesive layer 12 faces away from the tube, i.e., in the distal direction.

Distal terminal portion 22 has an annular surface 24 to which patch 10 is removably attached. More specifically, patch 10 adheres to surface 24 via the application of a vacuum or suction force via a tubular channel 26 extending longitudinally through applicator tube 18.

Prior to application of patch 10 to a tympanic membrane 14 (FIG. 5), the patch is manually positioned on surface 14 of applicator terminal portion 22. Suction is then applied at proximal end 20 of applicator tube 18. The proximal end of channel 26 is temporarily closed or sealed, e.g., by pressing a finger to the end of tube 18, to maintain the suction force, thereby holding tympanic patch 10 to distal end 22 of applicator tube 18 while tube 18 is being inserted through the auditory canal of a patient towards membrane 14. Upon a pressing of patch 10 against the ear drum or membrane 14, so that the patch covers the perforation 16, the proximal end 20 of tube 18 is released to pressurize channel 26 with ambient air. This pressurization releases patch 10 and allows the adherence of adhesive layer 12 to tympanic membrane 14.

Applicator tube 18 is made of a stiff material such a a metal or alloy having a limited malleability, whereby the tube may be reconfigured prior to the application of patch 10 to facilitate the positioning of the patch over perforation 16 in tympanic membrane 14.

Figure 2:
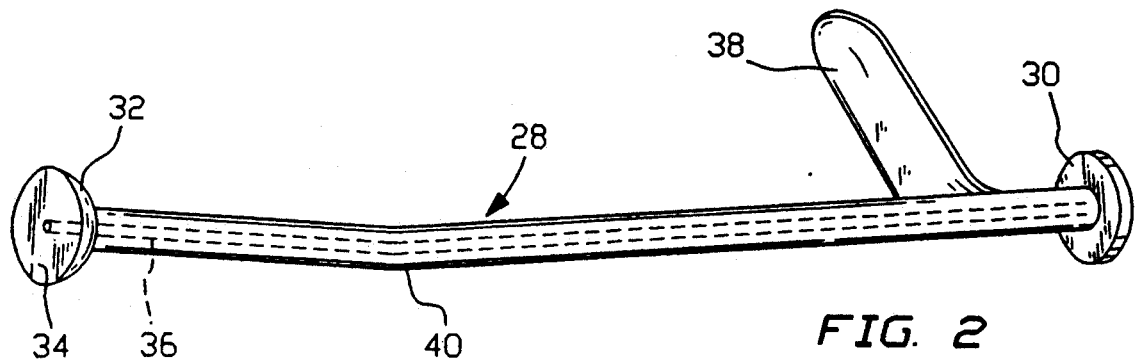
FIG. 2 is a schematic side perspective view, on an enlarged scale, of a modified applicator member in accordance with the present invention, for use with the patch of FIG. 1.

FIG. 2 shows another elongate applicator tube 28 having an enlarged proximal end portion 30 and an enlarged distal end portion 32. Patch 10 (FIG. 1) is removably attached to distal end portion 32 of applicator tube 28 so that adhesive layer 12 of patch 10 faces away from the tube, i.e., in the distal direction.

Distal end portion 32 has an annular surface 34 to which patch 10 is removably attached. More specifically, patch 10 adheres to surface 34 via the application of a vacuum or suction force via a tubular channel 36 extending longitudinally through applicator tube 28.

Proximal end portion 30 serves to facilitate the closing of channel 36 by a finger or thumb upon the application of a vacuum or suction to the channel. In addition, applicator tube 28 is formed with a finger grip 38 to facilitate the closure of channel 36 at proximal end portion 30.

Applicator tube 28 is also made of a stiff material such as a metal or alloy having a limited malleability. FIG. 2 shows tube 28 with a bend 40 to facilitate the positioning of patch 10 over perforation 16 (FIG.5) in tympanic membrane 14.

Figure 3:
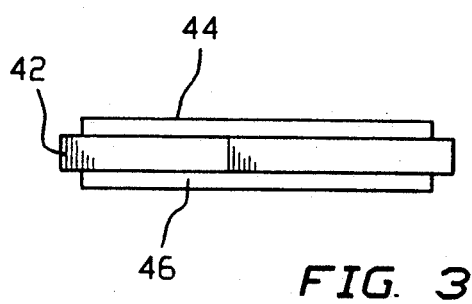
FIG. 3 is a side elevational view, on a substantially enlarged scale, of another tympanic patch in accordance with the present invention, which may be used with the applicator member of FIG. 1 or 2.

As illustrated in FIG. 3, a tympanic patch 42 may be provided on one side with an annular adhesive layer 44 for attaching the patch to a tympanic membrane to cover a hole therein. A second adhesive layer 46 is provided on the other side of patch 42 for releasably securing patch 42 to surface 24 of applicator terminal portion 22 or to surface 34 of distal end portion 32. Second layer 46 has an adhesiveness which is less than the adhesiveness of annular layer 44, whereby patch 42 may be removed from the applicator upon the pressing of patch 42 to a tympanic membrane.

To press patch 42 to a tympanic membrane, it is not necessary to apply suction to applicator tube 18 or 28. The temporary adherence of patch 42 to the applicator tub is implemented via secondary adhesive layer 46. Accordingly, channel 26 or 36 may be omitted, the respective applicator member taking the form of a rod, rather than a tube.

Figure 4:
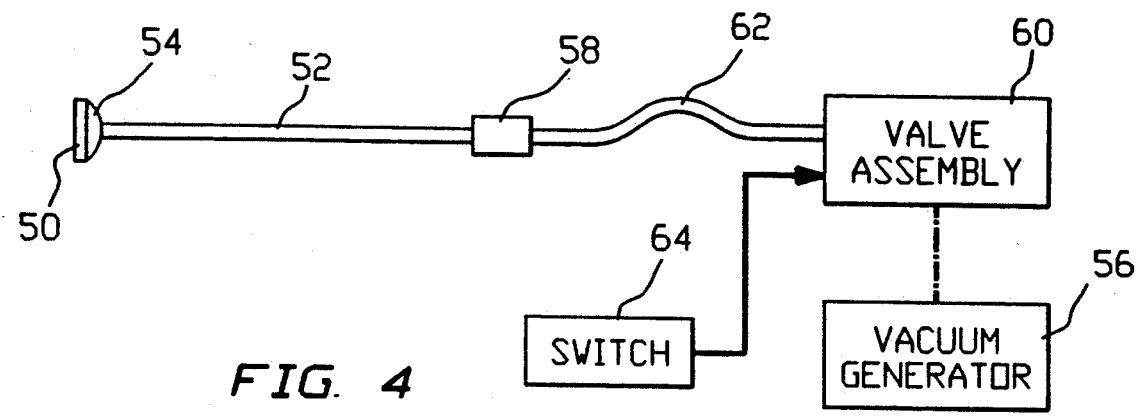
FIG. 4 is partially a side elevational view and partially a block diagram of a tympanic patch applicator system in accordance with the present invention.

As illustrated in FIG. 4, a system for applying a tympanic patch 50 comprises an elongate applicator tube 52 with an enlarged distal end portion 54. Patch 50 is temporarily held to end portion 54 by the application of suction from a vacuum generator 56 operatively connected to a coupling member 58 at a proximal end of applicator tube 52 via a valve assembly 60 and a hose 62. A switch 64 is operatively connected to valve assembly 60 for controlling the operation thereof to connect applicator coupling member 58 to vacuum generator 56 prior to a tympanic membrane repair operation and to disconnect the coupling member from the vacuum generator upon the pressing of patch 50 to a patient's tympanic membrane.

In repairing perforation 16 in tympanic membrane 14, patch 10 or 50 is pressed to the membrane so that the adhesive layer provided on the distal side of the patch (e.g., layer 12) adhesively engages the membrane in a region surrounding the perforation.

Patch 10 or 50 may be positioned manually on the distal end portion 22 or 32 prior to the insertion of the applicator tube 18 or 28 into a patient's auditory canal. Alternatively, during manufacture, patch 10 or 50 may be automatically placed on surface 24 or 34 of applicator member 18 or 28. In that event, the patch 10 or 50 and the respective applicator member is sold as a disposable unit. Similarly, the suction pressure in channel 26 or 36 may be implemented during manufacture, with a releasable sealing strip (not illustrated) attached to the proximal end of the applicator tube. Upon pressing of patch 10 or 50 against a tympanic membrane to cover a perforation therein, the sealing strip is manually removed, thereby allowing adherence of the patch to the perforated membrane.

Figure 6:
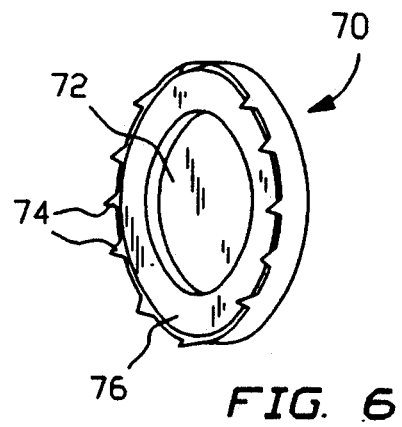
FIG. 6 is a schematic perspective view, on a greatly enlarged scale, of another tympanic patch in accordance with the present invention.

As illustrated in FIG. 6, a patch 70 for repairing a perforation in a tympanic membrane comprises disk shaped main body member 72 provided along its periphery with a plurality of angularly spaced barbs or teeth 74 which extend out of the plane of the disk shaped main body member 72 to one side thereof. On that side, main body member 72 is further provided with an annular adhesive layer 76. Although it is possible to provide a tympanic patch without an adhesive layer and to rely on barbs 74 alone to bind the patch to an ear drum, it is preferred to include an adhesive layer. As discussed hereinabove with reference to FIG. 3, a reverse side of main body 72 may be provided with an auxiliary adhesive layer for removably attaching patch 70 to the distal end of an applicator member.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A device for repairing a tympanic membrane, comprising:
    a patch;
    fastening means including an adhesive layer provided on one side of said patch for securing said patch to a tympanic membrane; and
    an elongate tubular applicator member having a proximal end and a distal end, said patch being removably attached to said distal end of said elongate applicator member, said fastening means facing away from said elongate applicator member, said applicator member defining an elongate channel susceptible to the application of suction and covered at said distal end by said patch.

2. The device defined in claim 1 wherein said adhesive layer is annular and said patch is circular.

3. The device defined in claim 1 wherein said elongate applicator member is formed at said distal end with an enlarged terminal portion.

4. The device defined in claim 3 wherein said terminal portion has an annular surface, said patch being removably attached to said annular surface.

5. The device defined in claim 1 wherein said elongate applicator member is made of a material having a limited malleability.

6. A method for repairing a perforation in a tympanic membrane, comprising the steps of:
    providing a patch having fastening means on one side for securing the patch to a tympanic membrane;
    removably attaching said patch to a distal end of an elongate tubular applicator member so that said fastening means faces away from said applicator member;
    applying suction to said applicator member to hold said patch to said distal end;
    inserting said distal end of said applicator member into an auditory canal towards the tympanic membrane to be repaired;
    pressing said patch to the tympanic membrane with said applicator member so that said fastening means engages the membrane in a region surrounding the perforation in the membrane; and
    removing the suction on said applicator member upon initiation of said step of pressing.

7. The method defined in claim 6 wherein said elongate applicator member is formed at said distal end with an enlarged terminal portion, said patch being removably attached to said terminal portion during said step of attaching.

8. The method defined in claim 6 wherein said elongate applicator member is made of a material having a limited malleability, further comprising the step of bending said elongate applicator member prior to said step of inserting, thereby optimizing a positioning of said patch over the perforation in the tympanic membrane.

9. A method for repairing a perforation in a tympanic membrane, comprising the steps of:
    providing a patch having fastening means on one side for securing the patch to a tympanic membrane;
    removably attaching said patch to a distal end of an elongate applicator rod so that said fastening means faces away from said applicator rod, said elongate applicator rod being made of a material having a limited malleability;
    bending said applicator rod, thereby optimizing a subsequent positioning of said patch over the perforation in the tympanic membrane;
    upon completion of said step of bending, inserting said distal end of said applicator rod with said patch into an auditory canal towards the tympanic membrane to be repaired;
    pressing said patch to the tympanic membrane with said applicator rod so that said fastening means engages the membrane in a region surrounding the perforation in the membrane; and
    upon completion of said step of pressing, disengaging said applicator rod from said patch, while leaving said patch attached to the tympanic membrane to be repaired.

* * * * *